United States Patent [19]

Chow et al.

[11] Patent Number: 4,515,810

[45] Date of Patent: May 7, 1985

[54] COMPOSITION OF MATTER

[75] Inventors: San-Laung Chow, Nanuet; Bernard Sims, Monsey, both of N.Y.

[73] Assignee: American Cyanamid Company, Stamford, Conn.

[21] Appl. No.: 539,450

[22] Filed: Oct. 6, 1983

[51] Int. Cl.³ .............................................. A61K 31/22
[52] U.S. Cl. ..................................... 514/530; 514/940
[58] Field of Search ............... 424/238, 243, 305, 317, 424/314

[56] References Cited

U.S. PATENT DOCUMENTS

| | | | |
|---|---|---|---|
| 4,211,793 | 7/1980 | Lodhi et al. | 424/305 |
| 4,370,322 | 1/1983 | Busse et al. | 424/243 |
| 4,396,615 | 8/1983 | Petrow et al. | 424/242 |
| 4,409,239 | 10/1983 | Yu | 424/305 |
| 4,431,833 | 2/1984 | Lodhi et al. | 424/305 |

Primary Examiner—Elbert L. Roberts
Attorney, Agent, or Firm—Anne M. Rosenblum

[57] ABSTRACT

A pharmaceutical composition of matter useful as a topical medicament which comprises an E-type prostaglandin compound or other water unstable active ingredient in a quick-breaking foam formulation to be dispensed from a pressurized container through a metered valve.

15 Claims, No Drawings

COMPOSITION OF MATTER

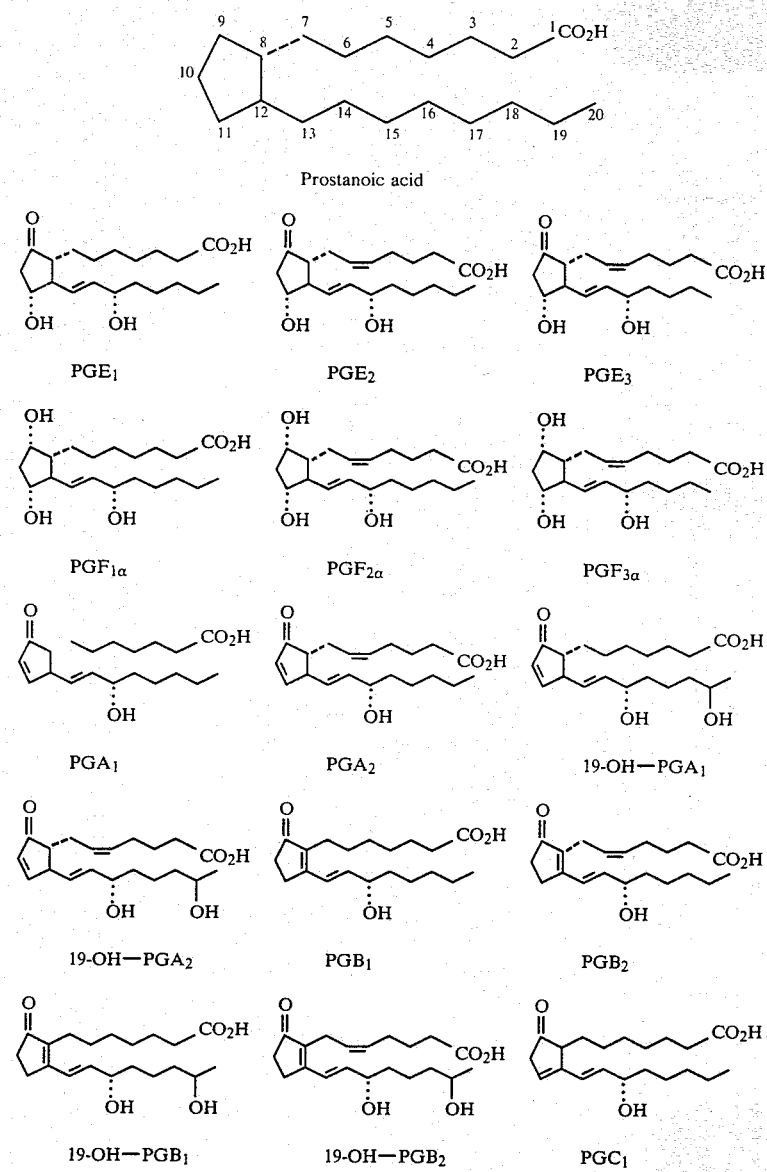

BACKGROUND OF THE INVENTION

1. Field of the Invention

The present invention relates to a pharmaceutical composition of matter which comprises an E-type prostaglandin compound or other water unstable active ingredient in a quick-breaking foam formulation to be dispensed from a pressurized container through a metered valve.

2. Description of the Prior Art

Prostaglandins are a group of closely related carboxylic acids containing a cyclopentane ring with two adjacent carbon side chains, one of which bears the carboxyl group at the terminal position. Most of the naturally occurring prostaglandins may be regarded as derivatives of the parent structure prostenoic acid. Natural prostaglandins are divided into four groups and although these may be named in accordance with their relationship to prostenoic acid, they are more conveniently referred to by the letters A, B, E, and F (shown below): all four groups have in common a trans=13,14 position bond, and a hydroxyl group at $C_{15}$.

Further, the E- and F-type possess an additional hydroxyl at $C_{11}$, with the E-type bearing a carbonyl function at $C_9$ while the F-type bears an hydroxyl at $C_9$.

Prostaglandins of the E-type and their esters are extremely potent in causing various biological responses and, for this reason, are useful for pharmacological purposes. Among these purposes are use as hypotensives, antilipodemics, bronchodilators, fertility control agents, and gastric secretion inhibitors. Bergstrom, et al., Pharmacol. Rev. 20:1 (1968) and the references cited therein. See also, U.S. Pat. Nos. 3,069,322 and 3,598,858 concerning esters of prostaglandins of the E-type. The basic problem in the pharmacological utilization of these drugs occurs in the relatively unstable nature of prostaglandin-like compounds of the E-type in conventional pharmaceutical formulations. These compounds tend to decompose, at and above room temperature, and in the presence of small amounts of acid or base.

For example, PGE$_2$ changes to PGA$_2$ in the presence of acid, while PGE$_2$ changes to PGB$_2$ in the presence of base. Similarly, other prostaglandin-like compounds of the E-type change to their corresponding compounds of the A- and B-type. In general, it can be said that the E-type prostaglandins may be distinguished from A- and B-type prostaglandins by the presence of hydroxyl at C$_{11}$ (shown below), and the A and B types may be regarded as dehydration products of E-type compounds resulting from a removal of the C$_{11}$ hydroxyl and the formation of a double bond in the ring.

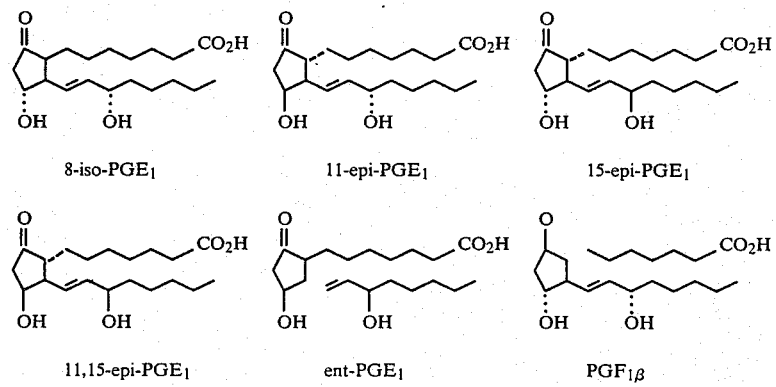

8-iso-PGE$_1$   11-epi-PGE$_1$   15-epi-PGE$_1$ 11,15-epi-PGE$_1$   ent-PGE$_1$   PGF$_{1\beta}$ Even in neutral aqueous solution or in a neat state there is a gradual change for E-types to A-types and B-types. Stability of the E-types has been observed in some solutions and in solid form at $-20°$ C. or lower but storage at this temperature is impractical and administration to mammals practically impossible. Better success at stabilizations have been obtained with other solutions and compositions as described in U.S. Pat. Nos. 3,749,800; 3,826,823; 3,829,579 and 3,851,052 and by Srivastava et al., Lipids, 8:592 (1973), wherein ethyl acetate, chloroform, and ethanol are used as solvents for prostaglandins of the E-types. Such solvents, however, are unsuitable for pharmaceutical dosage forms without dilution with water which causes rapid decomposition. A quantization of such decomposition may be found in Table I.

TABLE I

| | Percent E-type Prostaglandin degraded* | |
|---|---|---|
| Time (days) | Control | Triethyl citrate |
| 0 | 0% | 0% |
| 2 | 45% | not detectable |
| 4 | 80% | not detectable |
| 6 | | 1-2% |
| 14 | | 5-10% |

*70° C.

Prostaglandins and prostaglandin-like compounds of the E-type can be dissolved in the normally liquid substance known as triethyl citrate to provide an unexpectedly stable and useful pharmaceutical dosage form for the direct administration to warm-blooded animals. U.S. Pat. No. 4,211,793 describes the ability of triethyl citrate to retard the degradation and dehydration of prostaglandin E-type.

SUMMARY OF THE INVENTION

This invention relates to a new pharmaceutical composition of matter useful as a topical medicament which comprises an E-type prostaglandin compound or other water unstable active ingredient in a quick-breaking foam formulation to be dispensed from a pressurized container through a metered valve.

DETAILED DESCRIPTION OF THE INVENTION

The fundament of the instant invention resides in the discovery that E-type prostaglandin compounds and other water unstable compounds can be dissolved in a plasticizer such as triethyl citrate or diisopropyl adipate together with an emulsifying wax to provide an unexpectedly stable and pharmaceutically useful quick-breaking foam formulation for topical administration of the active ingredient to mammals.

In accordance with the present invention, there is provided a quick-breaking foam formulation for topical delivery of a medicament, which formulation is represented by the following Formula I:

| Formula I | |
|---|---|
| Emulsifying wax, N.F. | 2-10% |
| Plasticizer | 80-95% |
| Absolute ethanol (optional) | 1-10% |
| Active ingredient | — |

In the above formula, a particularly preferred emulsifying wax, N.F., is Polawax ® Regular or Polawax-®A.31 (sold by Croda Inc., 51 Madison Ave., New York, N.Y.) which are mixtures of higher fatty alcohols and ethylene oxide reaction products and conform to the National Formulary specifications for "Emulsifying Wax, N.F." (cetostearyl alcohol containing a polyoxyethylene derivative of a fatty acid ester of sorbitan). A particularly preferred plasticizer is triethyl citrate. For the active ingredient, of major interest as a topical vasodilator the prostaglandin 7-[2β-(4-butyl-4-hydroxy-1,5-hexadienyl)-3α-hydroxy-5-oxo-1α-cyclopentyl]-5-heptenoic acid, methyl ester, which is disclosed in U.S. Pat. No. 4,198,521, is particularly preferred in a sufficient amount to provide from 30–60 mcg per 35–120 mg dose with a preferred range of 30–60 mcg per 60 mg dose.

As a preferred embodiment the above formulation would contain 9.96 g of triethyl citrate; 0.66 g of Polawax ®; 0.86 g of absolute ethanol and 11.5 mg of the above-named prostaglandin per container.

The present invention further concerns a foam system for water unstable compounds as illustrated by the following Formula II:

| Formula II | |
|---|---|
| Emulsifying wax, N.F. | 10–20% |
| Mineral oil | 70–90% |
| Diisopropyl adipate | 5–20% |
| Active ingredient | — |

In Formula II, Polawax ® (Regular or A.31) is the preferred emulsifying wax. Alternatively, 5–10% of Promulgen-D ® (a mixture of 75% cetostearyl alcohol and 25% ethoxylate cetostearyl alcohol sold by Amerchol Corp., P.O. Box 351, Edison, N.J.) and 5–10% of Promulgen-G ® (a mixture of 75% stearyl alcohol and 25% ethoxylated cetostearyl alcohol sold by Amerchol Corp.) can be substituted for the Polawax ®. The same amount of Promulgen-D ® and Promulgen-G ® would be selected, as illustrated in the following Formula III:

| Formula III | |
|---|---|
| Diisopropyl adipate | 5–20% |
| Mineral oil | 70–90% |
| Promulgen-D ® | 5–10% ⎫ in equal |
| Promulgen-G ® | 5–10% ⎭ amounts |
| Active ingredient | — |

The amount of the active ingredient in the above Formulas I, II and III depends upon the topical dosage range of the particular drug to be incorporated into the foam system and the specific dose desired to be delivered onto the site.

The active ingredient intended for the foam system of this invention comprises water unstable compounds which dissolve in triethyl citrate or diisopropyl adipate. For instance, the E-type prostaglandin compound is particularly suitable for this system. Examples of PGE compounds are found in U.S. Pat. Nos. 3,069,322; 3,598,858; 4,061,670; 4,198,521; 4,254,285 and 4,299,988.

The E-type prostaglandin compounds cause localized vasodilation upon topical administration at very low doses. This activity causes an increased blood flow to the site of administration thereby accelerating the healing of wounds or burned tissue. Such action is also beneficial in the treatment of vascular occlusive and vasospastic diseases such as ischemic ulcers, scleroderma, acne, aged atrophic skin, psoriasis, ichthyosis, keratosis, pityriasis and related skin disorders.

In addition to PGE compounds, the scope of this invention is also intended to include other compounds that are soluble in triethyl citrate or diisopropyl adipate. Such pharmacological agents include, but are not limited to, topical corticosteroids such as triamcinolone 0.1% or amcinonide 0.1% for their anti-inflammatory, antipruritic and vasoconstrictive actions, topical anesthetics such as benzocaine 1%, and topical antibiotics such as tetracycline 3%.

As used with the foam formulation of the present invention, the term "quick-breaking" means that after delivery, as soon as the foam contacts the site of administration, the foam breaks up fast and disappears quickly leaving a thin-layered film on the site. The advantages of the foam system over a cream or an ointment are its neater appearance and it is easier to use than other topical preparations. The medication can be administered quickly and the proper dose can be effectively controlled via a metered valve. Other medication can be quickly applied at the same time.

The formulation of Formula I of this invention may be prepared according to the following general method: The active ingredient is dissolved in triethyl citrate by heating at 45°–70° C., preferably 55° C., on a steam bath with an emulsifying wax. Mixing must be thorough until both phases develop a clear solution together. The solution is cooled to room temperature. Absolute ethanol may then be added. Alternatively, mixing may be performed of individually heated solutions of an emulsifying wax and triethyl citrate containing the active ingredient.

The formulation of Formula II of this invention may be prepared according to the following general scheme: The emulsifying wax and mineral oil are mixed together on a steam bath at 45°–70° C., optimum at 55° C., to clear solution. The diisopropyl adipate containing dissolved active ingredient is mixed with the emulsifying wax-mineral oil mixture on a steam bath until a clear solution is obtained. The solution is cooled to room temperature.

Whereas the exact scope of the instant invention is set forth in the appended claims, the following specific examples illustrate certain aspects of the present invention. However, the examples are set forth for illustration only and are not to be construed as limitations on the present invention except as set forth in the appended claims.

A further understanding of the invention can be obtained from the following non-limiting preparations in the examples.

EXAMPLE 1

| Preparation of Formula I | |
|---|---|
| Polawax ® (Regular or A.31) | 0.66 g |
| Triethyl citrate | 9.96 g |
| 7-[2β-(4-butyl-4-hydroxy-1,5-hexadienyl)-3α-hydroxy-5-oxo-1α-cyclopentyl]-5-heptenoic acid, methyl ester | 11.5 mg |

11.5 mg of the above-named PGE, prepared according to the procedure in U.S. Pat. No. 4,198,521, was dissolved in 9.96 g of triethyl citrate by heating at 45°–70° C., preferably 55° C., on a steam bath together with 0.66 g of Polawax ® until a clear solution was obtained. The solution was cooled to room temperature, at about 23° C., producing an emulsion.

EXAMPLE 2

Preparation of Formula I (optional variation)

The method of Example 1 was followed. Into the resultant emulsion was stirred 0.86 g of absolute ethanol.

EXAMPLE 3

| Preparation of Formula I | |
|---|---|
| Polawax ® (Regular or A.31) | 0.66 g |
| Triethyl citrate | 9.96 g |
| 7-[2β-(4-butyl-4-hydroxy-1,5-hexadienyl)-3α-hydroxy-5-oxo-1α-cyclopentyl]-5-heptenoic acid, | 11.5 mg |

| Preparation of Formula I |
|---|
| methyl ester |

Individually heated on a steam bath at 45°–70° C., preferably 55° C., clear solutions of 0.66 g of Polawax ® and 9.96 g of triethyl citrate containing 11.5 mg of the above-named PGE (prepared according to the procedure in U.S. Pat. No. 4,198,521) were mixed at 45°–70° C., preferably 55° C., on a steam bath until a clear solution was obtained, and then cooled to room temperature, at about 23° C., producing an emulsion.

EXAMPLE 4

| Preparation of Formula II | |
|---|---|
| Diisopropyl adipate | 1.15 g |
| Mineral oil | 8.625 g |
| Polawax ® (Regular or A.31) | 1.725 g |
| 7-[2-β-(4-butyl-4-hydroxy-1,5-hexadienyl)-3α-hydroxy-5-oxo-1α-cyclopentyl]-5-heptenoic acid, methyl ester | 11.5 mg |
| | 11.5 mg |

1.725 g of Polawax ® and 8.625 g of mineral oil were mixed together on a steam bath at 45°–70° C., preferably 55° C., until a clear solution was obtained. Into 1.15 g of diisopropyl adipate was dissolved 11.5 mg of the above-named PGE, prepared according to the procedure in U.S. Pat. No. 4,198,521. On the steam bath at 45°–70° C., preferably 55° C., the diisopropyl adipate containing the PGE was mixed with the mineral oil/Polawax ® mixture until a clear solution was obtained. The solution was cooled to room temperature, at approximately 23° C., producing an emulsion.

EXAMPLE 5

| Preparation of Formula III | |
|---|---|
| Diisopropyl adipate | 1.15 g |
| Mineral oil | 8.625 g |
| Promulgen-D ® | 0.863 g |
| Promulgen-G ® | 0.863 g |
| 7-[2β-(4-butyl-4-hydroxy-1,5-hexadienyl)-3α-hydroxy-5-oxo-1α-cyclopentyl]-5-heptenoic acid, methyl ester | 11.5 mg |

The method of Example 4 was followed except for the substitution of the 0.863 g of Promulgen-D ® and 0.863 g of Promulgen-G ® for the Polawax ®.

EXAMPLE 6

Preparation of the Foam System

The respective mixtures of Examples 1–5 were separately filled into individual containers (either cans or plastic bonded aerosol bottles) together with an appropriate amount of propellant. As an example, 11.5 g of the emulsion and one gram of propellant were filled in a 23.6×75×20 mm can or 15 cc plastic bonded aerosol bottle. Suitable propellants include hydrocarbons such as propane, isobutane or mixtures thereof.

The cans are fitted with a metered valve which upon activation delivers a 35–120 mg (preferably a 60 mg) dose containing, depending upon the formulation, from 30–60 mcg of the above-named prostaglandin as a quick-breaking foam which adheres to the site and provides sustained release of the prostaglandin.

We claim:

1. A pharmaceutical composition of matter useful as a topical medicament which comprises a therapeutically effective amount of a water unstable E-type prostaglandin compound, 2–10% of emulsifying wax, N.F., and 80–95% of a plasticizer.

2. The pharmaceutical composition of matter according to claim 1, wherein the active ingredient is 7-[2β-(4-butyl-4-hydroxy-1,5-hexadienyl)-3α-hydroxy-5-oxo-1α-cyclopentyl]-5-heptenoic acid, methyl ester.

3. The pharmaceutical composition of matter according to claim 1, wherein the emulsifying wax is a mixture of higher fatty alcohols and ethylene oxide reaction products.

4. The pharmaceutical composition of matter according to claim 1, wherein the plasticizer is triethyl citrate.

5. A pharmaceutical composition of matter useful as a topical medicament which comprises a therapeutically effective amount of a water unstable E-type prostaglandin compound, 10–20% of emulsifying wax, N.F., 70–90% of mineral oil and 5–20% of diisopropyl adipate.

6. The pharmaceutical composition of matter according to claim 5, wherein the active ingredient is 7-[2β-(4-butyl-4-hydroxy-1,5-hexadienyl)-3α-hydroxy-5-oxo-1α-cyclopentyl]-5-heptenoic acid, methyl ester.

7. The pharmaceutical composition of matter according to claim 5, wherein the emulsifying wax is a mixture of higher fatty alcohols and ethylene oxide reaction products or equal parts of a mixture of 75% cetostearyl alcohol/25% ethoxylated cetostearyl alcohol and a mixture of 75% stearyl alcohol/25% ethoxylated cetostearyl alcohol.

8. A method of making a pharmaceutical composition of matter according to claim 1, comprising the steps of dissolving the water unstable E-type prostaglandin compound in the plasticizer by heating at 45°–70° C. on a steam bath together with the emulsifying wax until a clear solution is obtained, and cooling to room temperature.

9. A method of making a pharmaceutical composition of matter according to claim 1, comprising the steps of dissolving the water unstable E-type prostaglandin compound in the plasticizer by heating at 45°–70° C. on a steam bath together with the emulsifying wax until a clear solution is obtained, cooling to room temperature, and adding absolute ethanol.

10. A method of making a pharmaceutical composition of matter according to claim 1, comprising the steps of dissolving 7-[2β-(4-butyl-4-hydroxy-1,5-hexadienyl)-3α-hydroxy-5-oxo-1α-cyclopentyl]-5-heptenoic acid, methyl ester in triethyl citrate by heating at 45°–70° C. on a steam bath together with the emulsifying wax until a clear solution is obtained, and cooling to room temperature.

11. A method of making a pharmaceutical composition of matter according to claim 1, comprising the steps of dissolving 7-[2β-(4-butyl-4-hydroxy-1,5-hexadienyl)-3α-hydroxy-5-oxo-1α-cyclopentyl]-5-heptenoic acid, methyl ester in triethyl citrate by heating at 55° C. on a steam bath together with the emulsifying wax until a clear solution is obtained, and cooling to room temperature.

12. A method of making a pharmaceutical composition of matter according to claim 1, comprising the steps of mixing on a steam bath at 45°–70° C. individually heated on a steam bath at 45°–70° C. clear solutions of the emulsifying wax and the plasticizer containing the E-type prostaglandin compound until a clear solution is obtained, and cooling to room temperature.

13. A method of making a pharmaceutical composition of matter according to claim 1, comprising the steps of mixing on a steam bath at 55° C. individually heated on a steam bath at 55° C. clear solutions of the emulsifying wax and triethyl citrate containing 7-[2β-(4-butyl-4-hydroxy-1,5-hexadienyl)-3α-hydroxy-5-oxo-1α-cyclopentyl]-5-heptenoic acid, methyl ester until a clear solution is obtained, and cooling to room temperature.

14. A method of making a pharmaceutical composition of matter according to claim 5, comprising the steps of mixing together the emulsifying wax and mineral oil on a steam bath at 45°–70° C. until a clear solution is obtained, dissolving the E-type prostaglandin compound in the diisopropyl adipate on a steam bath at 45°–70° C., mixing the emulsifying wax/mineral oil mixture with the diisopropyl adipate containing the active ingredient on a steam bath at 45°–70° C. until a clear solution is obtained and cooling to room temperature.

15. A method of making a pharmaceutical composition of matter according to claim 5, comprising the steps of mixing together the emulsifying wax and mineral oil on a steam bath at 55° C. until a clear solution is obtained, dissolving 7-[2β-(4-butyl-4-hydroxy-1,5-hexadienyl)-3α-hydroxy-5-oxo-1α-cyclopentyl]-5-heptenoic acid, methyl ester in the diisopropyl adipate on a steam bath at 55° C., mixing the emulsifying wax/mineral oil mixture with the diisopropyl adipate containing the active ingredient on a steam bath at 55° C. until a clear solution is obtained and cooling to room temperature.

* * * * *